United States Patent
Barth et al.

(10) Patent No.: US 10,674,934 B2
(45) Date of Patent: Jun. 9, 2020

(54) APPARATUS AND METHOD FOR DETERMINING POSITIONAL INFORMATION FOR A MEDICAL INSTRUMENT

(71) Applicant: SIEMENS AKTIENGESELLSCHAFT, Munich (DE)

(72) Inventors: Karl Barth, Hoechstadt (DE); Rainer Graumann, Hoechstadt (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 798 days.

(21) Appl. No.: 14/108,588

(22) Filed: Dec. 17, 2013

(65) Prior Publication Data
US 2014/0171789 A1    Jun. 19, 2014

(30) Foreign Application Priority Data
Dec. 17, 2012    (DE) .................. 10 2012 223 418

(51) Int. Cl.
*A61B 5/06*    (2006.01)
*A61B 34/20*    (2016.01)

(52) U.S. Cl.
CPC .............. *A61B 5/062* (2013.01); *A61B 34/20* (2016.02); *A61B 2034/2051* (2016.02)

(58) Field of Classification Search
CPC ....... A61B 5/062; A61B 5/06; A61B 19/5225; A61B 19/5244; G01R 33/285
USPC ....................................................... 600/424
See application file for complete search history.

(56) References Cited

U.S. PATENT DOCUMENTS

| | | | | |
|---|---|---|---|---|
| 5,913,820 A | * | 6/1999 | Bladen ..................... | A61B 5/06 128/899 |
| 6,073,043 A | * | 6/2000 | Schneider ................ | A61B 5/06 128/899 |
| 2006/0025668 A1 | | 2/2006 | Peterson et al. | |
| 2008/0054887 A1 | * | 3/2008 | Lee ..................... | G01D 5/2053 324/207.17 |
| 2008/0204004 A1 | * | 8/2008 | Anderson .............. | A61B 90/36 324/207.13 |

(Continued)

OTHER PUBLICATIONS

Nishida et al., "3D Ultrasonic Tagging System for Observing Human Activity", Proceedings of the 2003 IEEE, RSJ, Intl. Conference on Intelligent Robots and Systems, Las Vegas, Nevada, Oct. 2003, pp. 785-791.*

*Primary Examiner* — Katherine L Fernandez
(74) *Attorney, Agent, or Firm* — Laurence Greenberg; Werner Stemer; Ralph Locher (57) ABSTRACT

An apparatus and a method for determining the position of a medical instrument, particularly for the purpose of medical navigation. In order to use a simple system to provide a relatively inexpensive technique for determining positional information, the position and/or orientation of the medical instrument is determined by ascertaining the same on the basis of position finding operations. Electromagnetic fields are first measured and the results of relative field strength measurements are taken as a basis for ascertaining the direction of a line from a transmitter to a receiver. After this direction information is known, it is used to determine the positional information of the medical instrument.

18 Claims, 2 Drawing Sheets

(56) References Cited

U.S. PATENT DOCUMENTS

2011/0066029 A1\* 3/2011 Lyu .................. A61M 25/0133
600/424
2014/0002063 A1\* 1/2014 Ashe .................... A61B 8/4254
324/207.15

\* cited by examiner

APPARATUS AND METHOD FOR DETERMINING POSITIONAL INFORMATION FOR A MEDICAL INSTRUMENT

CROSS-REFERENCE TO RELATED APPLICATION

This application claims the priority, under 35 U.S.C. § 119, of German patent application DE 10 2012 223 418.7, filed Dec. 17, 2012; the prior application is herewith incorporated by reference in its entirety.

BACKGROUND OF THE INVENTION

Field of the Invention

The invention relates to an apparatus and a method for determining the position and situation of a medical instrument, particularly for the purpose of medical navigation.

Image-guided interventions are known from the prior art. Nowadays, such processes are part of clinical routine. In contrast to invasive surgical treatment, minimally invasive image-guided interventions allow the user to work with minimal injury to the patient and faster healing. This also reduces the risk of complications, has a positive cosmetic effect and lowers clinical costs.

The performance of image-guided interventions often requires medical instruments to be navigated inside the body of the patient. In this case, the term "medical navigation" is understood to mean determining the position by means of localization, planning the access path to the destination and guiding a medical instrument to this destination on the planned access path. It is known practice to put reference markings on the body of the patient or on the medical instrument to this end. By way of example, these may be visual markings, for example three-dimensional markers that can be captured by a stereo camera, or else electromagnetic markings, for example coils that can be excited in an electromagnetic field. The reference markings can then be used to determine the situation of the medical instrument relative to the body of the patient and to use the situation for navigation.

In the case of electromagnetic systems, a coil arrangement is used to produce an exactly defined electromagnetic field at the location of the instrument. A receiver on the instrument picks up the field by using sensor coils and transmits the field strength to a processing unit. From the field strength, the processing unit calculates the position and the orientation of the instrument by ascertaining the distance of the instrument from the coil arrangement that produces the electromagnetic field. For this purpose, firstly high-precision sensor coils and secondly a high-precision and constant magnetic field that has a defined, known field profile are required. Just extremely small disturbances in the magnetic field, for example as a result of inadequately shielded third-party appliances, result in an unknown alteration in the field profile and hence in errors in the situation determination for the instrument. The provision of the high-precision sensor coils and of the defined electromagnetic field and the avoidance of disturbing influences are complex and expensive.

SUMMARY OF THE INVENTION

It is accordingly an object of the invention to provide a method and a device for determining the positional situation of a medical instrument which overcome the above-mentioned disadvantages of the heretofore-known devices and methods of this general type and which provides for simple means to provide a technique for situation determination that is less sensitive to disturbance and is also less expensive.

With the foregoing and other objects in view there is provided, in accordance with the invention, an apparatus for determining positional information of a medical instrument, the apparatus comprising:
 a processing unit,
 a number of first components configured to produce electromagnetic fields;
 a number of second components disposed and configured to measure the electromagnetic fields produced by said first components and to transmit respective measurement results to said processing unit;
 said processing unit being configured to:
 ascertain direction information by way of direction finding based on the measurement results; and
 determine at least one of a position or an orientation of at least one first component or at least one second component by using the ascertained direction information.

The term "positional information" is understood, in the context of this description, to include the concepts of position and/or location and also of orientation. The medical instrument is thus monitored to determine its position in the monitored space and also its orientation in the monitored space.

It is a central concept of the invention to determine the situation that is to say to determine the position and/or orientation of the medical instrument relative to a reference system, by no longer performing distance measurement. Instead, the position and/or the orientation of the instrument is/are determined on the basis of direction finding operations. To this end, electromagnetic fields are first of all measured and the results of relative field strength measurements are taken as a basis for ascertaining the direction of a line from a transmitter to a receiver. After this direction information is known, it is used to determine the situation of the medical instrument. For this purpose, the point of intersection of the direction finding lines is ascertained, in a manner which is fundamentally known to a person skilled in the art.

Since just direction finding operations and no distance measurements are required, the demands on the field that is emitted are comparatively low. The field strength does not need to be constant, nor does the local field profile need to be known. It is merely necessary for the field strengths that are measured for the purpose of direction finding to be large enough to obtain an evaluable measurement signal. Disturbances can be accepted so long as any evaluable signal continues to be measurable. The proposed method therefore has a high level of disturbance immunity.

Overall, the complexity for providing the field to be measured is much lower than in the case of the methods known from the prior art. At the same time, the field no longer has to be maintained over a relatively long measurement period. The emission of temporally limited field pulses or field pulse sequences is adequate. In other words, the field does not exist continuously, but rather is switched on and off in a particular rhythm. Usually, the emission of a single short pulse is sufficient for direction finding. Furthermore, it is also no longer necessary to use high-precision receivers. Instead, simple and hence inexpensive receivers can be used.

The situation is determined relative to a reference system. The reference system is stipulated by the immovable components of the inventive apparatus. The reference system is preferably a navigation space, that is to say a local area in which the medical navigation takes place. The immovable components are advantageously placed such that they distally bound the navigation space and enclose the measurement area.

The coordinate system associated with the navigation space may be defined relative to the table plane of an operating table, for example. In this case, the navigation space encompasses a defined local area above the operating table. In this example, the situation of the medical instrument can be determined relative to the operating table. By adding further coordinate systems, knowledge of the relationships of the systems relative to one another allows the situation of the instrument relative to any other reference system to be determined. By way of example, it is thus possible to determine the situation of the instrument relative to an object that is located on the operating table if the situation of the object relative to the operating table is known.

Preferably, the inventive apparatus is used as part of a system for medical navigation. For this purpose, the individual components may be permanently or intermittently connected to medical instruments and other medical devices, such as an operating table, and/or arranged in a space. The inventive apparatus, as part of a medical navigation system, is advantageously connected to a display device that is used to show the position and/or orientation of the medical instrument.

In a first embodiment of the invention, at least two immovable transmitter assemblies (transmitter groups) and a number of receiver assemblies (receiver groups) arranged on the instrument are used. In this case, each transmitter assembly forms a source location, and each receiver assembly forms a reception location. The situation of the instrument is in this case determined relative to a reference system that is stipulated by the immovable transmitters of the transmitter assemblies.

The at least one receiver assembly is placed in a fixed physical relationship with a medical instrument, in particular arranged in or on the instrument. The receiver assembly is to be understood as a grouping of receivers and comprises at least two receivers, particularly sensor coils for picking up the magnetic field. For the purpose of implementing the invention, at least one receiver assembly is required. If a plurality of receiver assemblies per instrument are used, in particular at a distance from one another on different portions of the instrument, it is possible for the reliability and precision of the situation determination to be increased and/or it is possible, according to the placement of the receiver assemblies, to determine the situation of different portions of the medical instrument independently of one another.

Each receiver assembly is designed not only to measure the magnetic fields produced but also to transmit the measurement results to the processing unit. In this case, the measurement results can, depending on the embodiment, be transmitted by wire or wirelessly.

In order to produce the magnetic fields, at least two spaced-apart transmitter assemblies are provided. Each transmitter assembly is intended to be understood as a grouping of transmitters and comprises a number of transmitters. The transmitters are arranged at defined locations and are designed to produce magnetic pulses, that is to say signals at particular intervals. Preferably, each transmitter can be actuated individually for this purpose. In this case, each transmitter is designed to produce a field having a known, defined orientation. In this case, a transmitter is actuated such that it produces magnetic pulses at particular intervals. If a plurality of transmitters are provided, these are preferably actuated such that they successively produce magnetic pulses. However, provision may also be made for a plurality of transmitters to produce magnetic pulses simultaneously.

In order to perform the situation determination, magnetic pulses are sent from different locations in temporal succession. The field strength of these magnetic pulses is measured by at least two receivers of a receiver assembly. Since the relative field strength is dependent on the direction of the receiver in relation to the transmitter, the processing unit uses common vectorial consideration of the measurement signals to ascertain the direction or at least a direction component from the receiver to the respective transmitter. The common point of intersection of these direction lines is used to ascertain the position of the receiver. In other words, direction finding is taken as a basis for performing localization or situation determination, that is to say the determination of the position and/or orientation of the receiver. From the position and/or orientation of the at least two receivers of a receiver assembly, the processing unit determines the position and/or the orientation of the receiver assembly and hence the situation of the reception location. Since the receiver assembly is placed in or on the instrument in a known and defined manner, it therefore also determines the position and/or orientation of the medical instrument itself.

In a second embodiment of the invention, at least one mobile transmitter assembly (transmitter group) is used together with a plurality of immovable receiver assemblies (receiver groups). In this case, each transmitter assembly again forms a source location and each receiver assembly forms a reception location. In this case, the situation of the instrument is determined relative to a reference system that is stipulated by the immovable receivers of the receiver assemblies.

Since the situation of the at least one transmitter assembly is intended to be determined in this case, said transmitter assembly is placed in a fixed physical relationship with the medical instrument, in particular arranged in or on the instrument. The transmitter assembly comprises one or more transmitters that can again be actuated to produce magnetic pulses. Preferably, each transmitter can again be actuated individually. In this case, a transmitter is actuated such that it produces magnetic pulses at particular intervals. If a plurality of transmitters are provided, these are again preferably actuated such that they successively produce magnetic pulses. If a plurality of transmitter assemblies per instrument are used, in particular at a distance from one another on different portions of the instrument, it is possible to increase the reliability and precision of the situation determination and/or it is possible, according to the placement of the transmitter assemblies, to determine the situation of different portions of the medical instrument independently of one another.

At least two spaced-apart receiver assemblies arranged at defined locations are used that each comprises a number of receivers. The position and orientation of each receiver are known in this case. Again, each receiver assembly is designed not only to measure the magnetic fields produced but also to transmit the measurement results to the processing unit.

The transmitters are used to produce a succession of magnetic pulses. The field strength of each magnetic pulse sent from different locations is measured simultaneously by at least two receiver assemblies and hence by physically spaced receivers. The processing unit uses common vectorial consideration of the simultaneously induced measurement signals in the receivers to calculate the direction or at least a direction component of the position of the respective transmitters from each receiver position. The common point of intersection of these direction lines is used to ascertain the position of the respective transmitter. In other words, the direction finding is taken as a basis for performing localization or situation determination, that is to say the determination of the position and/or orientation of the transmitter. From this, the processing unit determines the position and/or the orientation of the transmitter assembly, and hence the situation of the source location and hence also the position and/or orientation of the medical instrument itself.

Under particular conditions, for example when the transmitter assembly associated with the instrument is always moved in one plane, for example at the same level, it is sufficient if the transmitter assembly comprises a single transmitter. With two or more transmitters per transmitter assembly, complete situation determination can take place, on the other hand.

Both in the case of the first and in the case of the second embodiment of the invention, the transmitters of the transmitter assemblies are preferably arranged directly adjacent to one another, as a result of which each transmitter assembly has as small a physical extent as possible. This is intended to produce an ideally punctiform source location. In this case, the transmitters cannot exceed a particular size in order to guarantee sufficient angle precision for the direction finding from a particular measurement distance onward.

The transmitters used are preferably generator coils. The use of very small coils, for example coils with a length or a diameter distinctly below 1 cm, may suffice. In these cases, coils with a large number of turns are preferably used. The generator coils are preferably arranged such that the coil axes of the generator coils in different coil arrangements are at least in part not situated parallel to one another. If a plurality of transmitters are used per transmitter assembly, the generator coils within a transmitter assembly are preferably arranged at right angles to one another and the generator coils of different transmitter assemblies are preferably arranged parallel or at right angles to one another. A parallel or right-angled arrangement facilitates the later calculation and ascertainment of the situation information.

Both in the case of the first and in the case of the second embodiment of the invention, sensor coils are used as receivers of the receiver assembly. For the receivers, the use of coils having a small number of turns can suffice. Thus, in the case of the arrangement of the sensor coils on the medical instrument, a coil having just a single turn encompassing the instrument may be sufficient, for example. The sensor coils of a receiver assembly are again preferably arranged such that their coil axes are not situated parallel to one another. Preferably, in this case too, the sensor coils within a receiver assembly are preferably arranged at right angles to one another and the sensor coils of different receiver assemblies are arranged parallel or at right angles to one another. A parallel or right-angled arrangement again facilitates the later calculation and ascertainment of the situation information.

If, in the first embodiment of the invention, more than the absolutely required transmitter assemblies, or, in the second embodiment of the invention, more than the required receiver assemblies, are used then it is possible for disturbances in a magnetic field to be recognized and compensated for. Furthermore, such use of redundant components allows the precision of the situation determination to be increased, for example by means of averaging of the results, statistical evaluation, square error minimization and/or by means of plausibility considerations and the rejection of implausible outliers. The processing unit is accordingly designed for this purpose.

Other features which are considered as characteristic for the invention are set forth in the appended claims.

Although the invention is illustrated and described herein as embodied in an apparatus and method for determining the situation of a medical instrument, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

All of the figures show the invention merely schematically and with its essential constituents. In this case, identical reference symbols correspond to elements having the same or a comparable function.

DETAILED DESCRIPTION OF THE INVENTION

Figure 1:
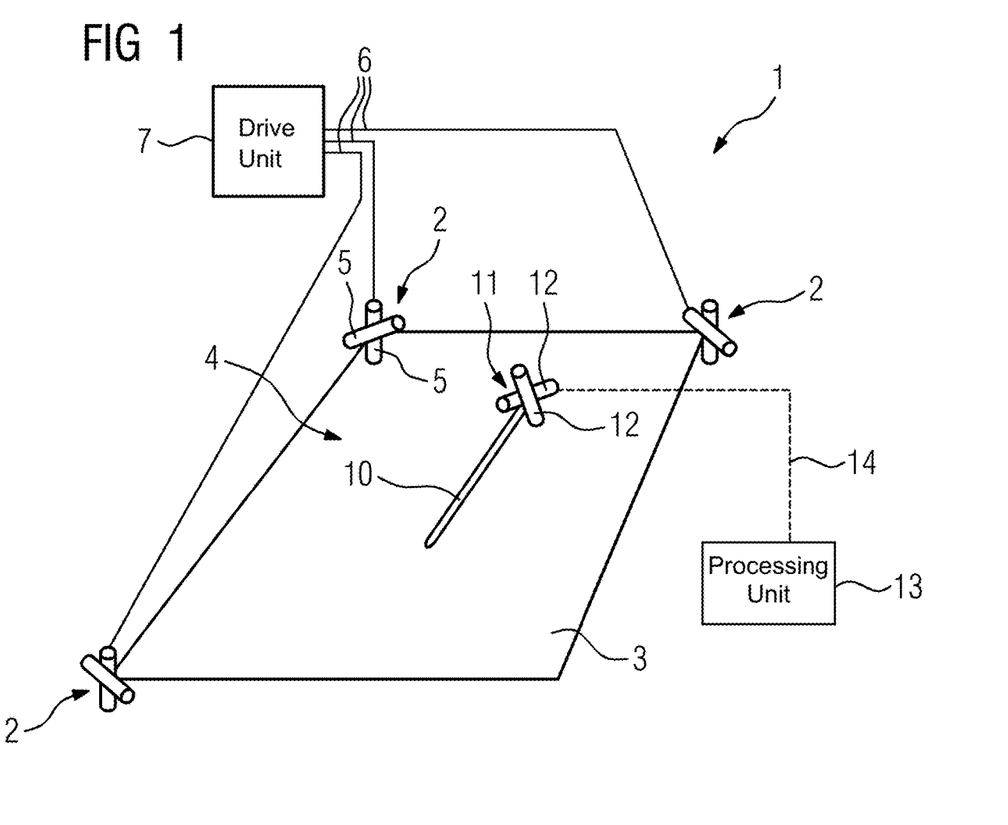
FIG. 1 is a schematic illustration of a first exemplary embodiment of the apparatus with immovable/stationary transmitters.

Referring now to the figures of the drawing in detail and first, particularly, to FIG. 1 thereof, there is shown a first exemplary embodiment of the novel apparatus. The apparatus 1 includes three transmitter assemblies 2 that are positioned at the corners of an area 3 of a patient's table and contain a navigation space 4 above the area 3. The area 3 is any work area on the patient's table which is suitable for navigation, in this case a rectangular work area, for example. However, the area may also have a different shape. The transmitter assemblies 2 also do not need to be located in the plane of the patient's table. By way of example, a number of transmitter assemblies 2 may be arranged in the table plane and/or a number of transmitter assemblies 2 may be arranged above or below the patient's table.

Each transmitter assembly 2 defines a source location. The transmitter assemblies 2 are at a minimum distance from one another that influences the desired precision of the later situation determination. Each transmitter assembly 2 comprises two transmitters, in the form of small generator coils 5, that are arranged directly adjacent and orthogonally at right angles to one another. Each of these generator coils 5 is used as a magnetic field generator and is configured to produce an electromagnetic field. The position and orientation of the generator coils 5 are known. The generator coils 5 are connected by way of connecting lines 6 to an actuating unit or drive unit 7. Instead of two, the transmitter assemblies 2 may also have three generator coils 5, for example. These are then preferably in turn arranged at right angles, but at any rate in a defined manner, in relation to one another.

A receiver assembly 11 is positioned on a freely movable medical instrument 10 that needs to be navigated. The receiver assembly 11 defines a reception location. The assembly 11 comprises two receivers, in the form of small sensor coils 12, that are arranged directly adjacent and orthogonally, at right angles to one another. Each sensor coil 12 is configure to measure an electromagnetic field and to transmit the measurement results to a processing unit 13. To this end, the sensor coils 12 are connected by means of a wireless link 14 to the processing unit 13. Instead of two, the receiver assemblies 11 may also have three sensor coils 12, for example. They are then preferably arranged orthogonally at right angles, but at any rate in a defined manner, in relation to one another.

In a modified embodiment, which is not specifically illustrated, the instrument 10 may carry more than one receiver assembly 11 in order to increase the precision of the location determination.

To determine the position of the instrument 10, the generator coils 5 of the three transmitter assemblies 2 are actuated in succession by the actuating unit 7 such that they produce short magnetic pulses. These may be single pulses or pulse trains, for example periodic pulse trains. The generator coils 5 can also be actuated in a different order so long as this order is known. Usually, a pulse is output by each transmitter assembly 2 once or multiple times for the purpose of position determination. If a transmitter assembly 2 contains a plurality of generator coils 5, a pulse is preferably output by each generator coil 5 of the transmitter assembly 2 once or multiple times.

The succession of short pulses that is produced in this manner is received by the (two) sensor coils 12 of the receiver assembly 11 that are arranged in a defined position relative to one another. The measurement results from this field strength measurement are transmitted from the sensor coils 12 to the processing unit 13. The processing unit 13, which knows the position and orientation of the generator coils 5, ascertains direction vectors for the respective source locations from the measurement results. In other words, the direction of source locations for a magnetic field is sequentially found. From at least two of these direction vectors, the processing unit 13 determines the location and the orientation of the respective sensor coil 12, and hence of the receiver assembly 11 and the instrument 10. In this case, the determination of the position by the processing unit 13 is based on the fact that for any orientation in space the signal received by a sensor coil 12 is always proportional to the direction cosine of the coil axis thereof with the local field line profile. It holds that $$S=\alpha*\cos(B),$$

where S denotes the received signal, B denotes the field strength and α (alpha) denotes the angle enclosed between the coil axis of the sensor coil 12 and the field line. The ratio of the cosines of the signal strengths of two sensor coils 12 at right angles, for example, therefore indicates a direction to the field line. Since only relative field strength measurements are performed for locally adjacent sensor coils 12, the absolute value of the field strength generated by the generator coils 5 does not have to meet any special precision requirements. Therefore, increased robustness and reliability are achieved for the method with relatively low complexity and relatively low costs.

In this case, the term "short magnetic pulses" is understood to mean pulses having a duration of distinctly shorter than one second. Preferably, the magnetic pulses used are so short that the transmitters of each transmitter assembly 2 produce magnetic pulses multiple times in one second. In other words, magnetic pulses are intended to leave each source location multiple times per second. Therefore, secure determination of the position of the instrument is possible even when the instrument is being moved. The magnetic pulses produced have a pulse duration of 10 milliseconds, for example.

Figure 2:
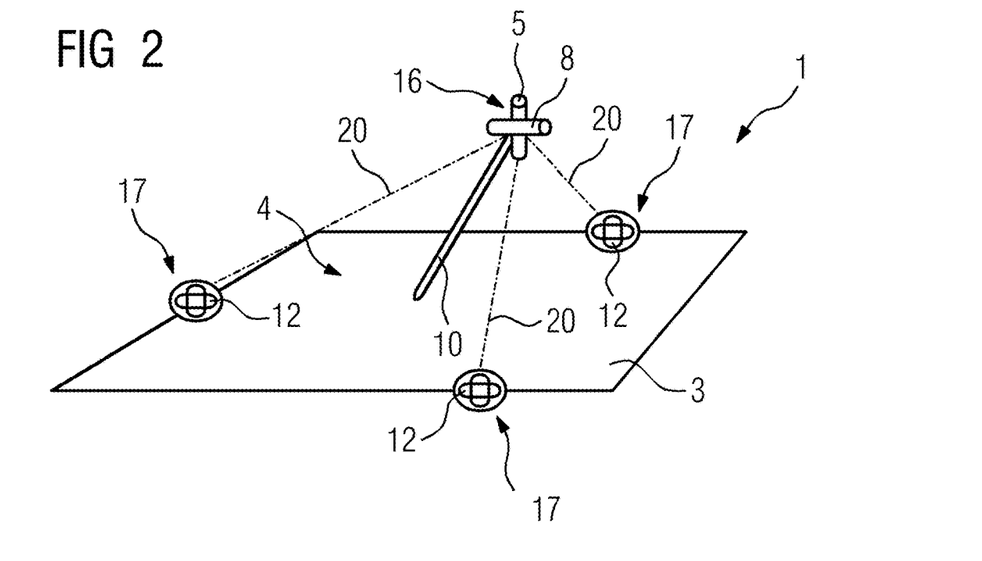
FIG. 2 is a schematic illustration of a second exemplary embodiment of the invention with immovable/stationary receivers.

Referring now to FIG. 2, a second exemplary embodiment of the novel apparatus according to the invention includes three receiver assemblies 17 that are positioned at the edges of an area 3 of a patient's table. Otherwise, substantially the same applies to the arrangement of the receiver assemblies in this second exemplary embodiment as to the arrangement of the transmitter assemblies in the first exemplary embodiment.

Each receiver assembly 17 defines a reception location. The receiver assemblies 17 are at a minimum distance from one another that influences the desired precision of the later situation determination. Each receiver assembly 17 comprises three receivers, in the form of small sensor coils 12, that are arranged directly adjacent and at right angles to one another. The position and orientation of the sensor coils 12 are known. Each sensor coil 12 is designed to measure an electromagnetic field and to transmit the measurement results to a processing unit 13. To this end, the sensor coils 12 are connected to the processing unit. In order not to clutter the illustration, the processing unit is not illustrated in FIG. 2.

A transmitter assembly 16 is positioned on a freely movable medical instrument 10 that is to be navigated. The transmitter assembly 16 defines a source location and comprises two transmitters, in the form of small generator coils 5, 8, that are arranged directly adjacent and orthogonally at right angles to one another. Each of these generator coils 5, 8 is used as a magnetic field generator and is designed to produce an electromagnetic field. The generator coils 5, 8 are connected to an actuating unit or drive unit—again, not illustrated in FIG. 2—which may also be arranged in or on the instrument 10.

Instead of two coils 5, 8, the transmitter assembly 16 may again have three generator coils. Also, the instrument 10 may carry more than one transmitter assembly 16.

To determine the positional information for the instrument 10, the generator coils 5 of the transmitter assembly 16 are actuated via the actuating unit 7 such that they successively produce short magnetic pulses. These may be single pulses or pulse trains, for example periodic pulse trains. The term short magnetic pulse has already been explained above in connection with the first exemplary embodiment.

In this case, the magnetic pulses are sent cyclically. Usually, each transmitter assembly 16 outputs a pulse once or multiple times for the purpose of situation determination. The succession of pulses that is produced in this manner is simultaneously received by all sensor coils 12 of the receiver assemblies 17. The measurement results from these field strength measurements are transmitted from the sensor coils 12 to the processing unit 13. The processing unit 13, which knows the position and orientation of the generator coils, ascertains direction vectors for the source location from the measurement results by means of direction finding. From at least two of these direction vectors, the processing unit 13 determines the location and the orientation of the respective generator coil 5, 8, and hence of the transmitter assembly 16 and the instrument 10.

With the two generator coils 5, 8 at right angles and the three simultaneously receiving sensor coils 12, arranged at right angles to one another, of one of the three receiver assemblies 17, the orientation of a generator coil 5, 8 in space is already defined and a bearing direction known. Using measurement results from further receiver assemblies 17, the processing unit 13 then determines the position of the generator coils 5, 8. Fundamentally, it holds that the sensor coils 12 have the defined rotation relative to one another in order to cover all three spatial directions. Preferably, they are arranged at right angles to one another, as in the present example.

Figure 3:
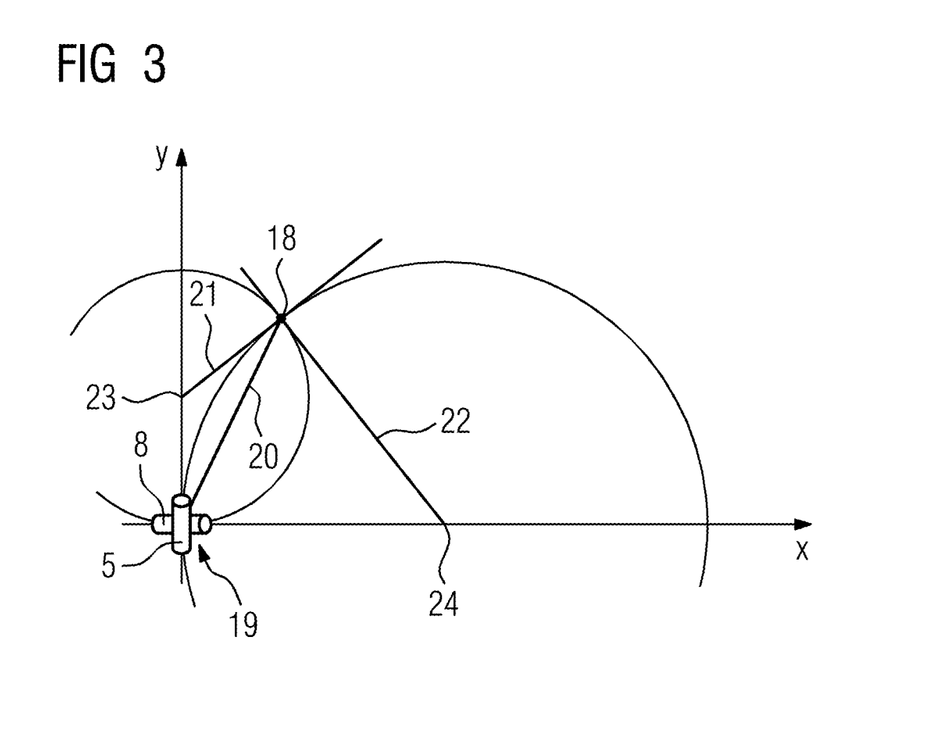
FIG. 3 is a first schematic illustration for direction finding.

The field lines of the two generator coils 5, 8 in the transmitter assembly 16 mounted on the instrument 10 intersect one another at right angles at each location, even in an identical direction of propagation, as shown in FIG. 3. For each transmitter coil 12 arranged at any location 18 relative to the source location 19, the processing unit 13 uses component-by-component vector consideration for a pulse from the first generator coil 5, which is arranged vertically in FIG. 3, to ascertain the field line direction 21 of said generator coil. The straight line 21 running through the location 18 of the sensor coil 12, which location is shown as a dot in FIG. 3, has the property that it also runs through the center 23 of the field line of the second generator coil 8, which is arranged horizontally in FIG. 3, which field line runs through the sensor coil 12 at the location 18. Following the reception of the further pulse emitted by this second generator coil 8, the processing unit 13 ascertains the field line direction 22 at the location 18 of the sensor coil 12, which field line direction points from there to the mathematical center 24 of the previously measured field line.

For the registered pulses, the sensor coils 12 also ascertain the respective field strength, and the processing unit 13 uses this to determine the ratio of the distances 25, 26 of the location 18 of the sensor coil 12 from the centers 23, 24 of the field lines.

Figure 4:
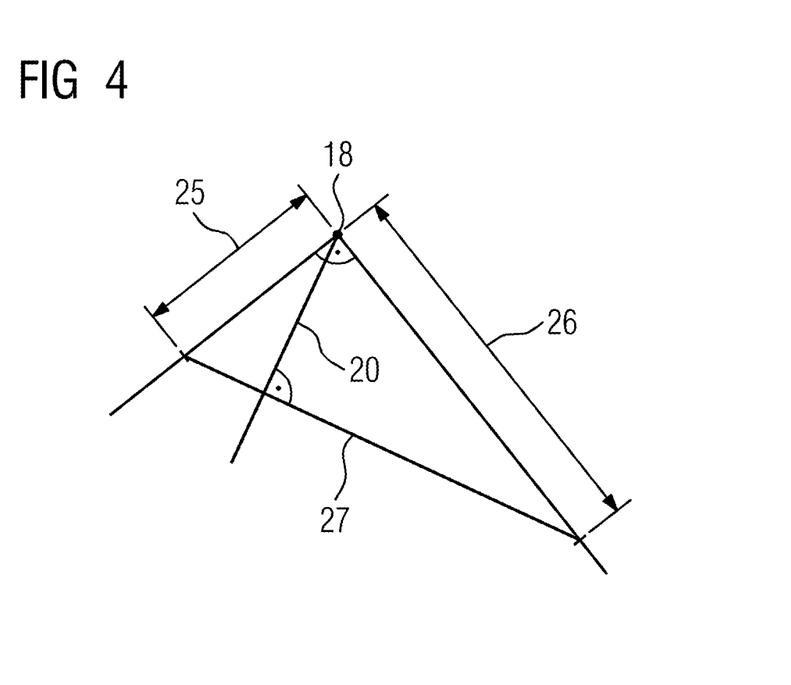
FIG. 4 is a second schematic illustration for direction finding.

These distances 25, 26 are removed by the processing unit 13 to the limbs of a right angle, so that, as illustrated in FIG. 4, a triangle with catheti 25 and 26 and a hypotenuse 27 is obtained, which is similar to that right-angled triangle that is formed by the points 18, 23 and 24. The height in this right-angled triangle runs in the sought direction 20 in which the source location 19 is seen from the location 18 of the currently considered sensor coil 12 when the field lines run in one plane. This calculation can be performed by the processing unit 13 in one plane.

The presentations in FIGS. 3 and 4 illustrate the circumstances in simplified fashion and merely by way of example for the case in which the field lines run in one plane. In a general case, the field line around the center 23 may also be arbitrarily rotated out of the plane of the drawing or into the plane of the drawing around the chord 20, for example. Fundamentally, the direction 20 can be described by using two angles, namely the angle between the cathetus 25 and the height ray 20 and also the angle between the cathetus 26 and the height ray 20. For the interpretation of these two angles by the processing unit 13, the general case requires the inclusion not of field lines situated in one plane but of another angle ("bend angle") between the field lines that is able to be used to describe the rotation of the field lines around the chord 20 serving as an axis of rotation. This achieves the object of direction finding in space.

An advantage of the inventive method is that it is only necessary to ascertain the directions of the catheti 21 and 22 and the ratio of the distances 25, 26 relative to one another.

The inventive apparatus 1 is designed to carry out the described method for determining the position (location, orientation) of a medical instrument 10 for the purpose of medical navigation. Preferably, the processing unit 13 of the apparatus is a data processing unit, designed to carry out all of the steps in accordance with the method described here that are related to the processing of data. The processing unit preferably has a plurality of functional modules, each functional module being configured to perform a particular function or a number of particular functions according to the described method. The functional modules may be hardware modules or software modules. In other words, the invention, insofar as it relates to the processing unit, can be implemented either in the form of computer hardware or in the form of computer software or in a combination of hardware and software. Insofar as the invention is implemented in the form of software, that is to say as a computer program product, all the functions described are realized by computer program instructions when the computer program is executed on a computer with a processor. In this case, the computer program instructions are implemented in any programming language in a manner that is known per se and can be provided for the computer in any form, for example in the form of data packets, which are transmitted via a computer network, or in the form of a computer program product that is stored on a floppy disk, a CD-ROM or another data storage medium.

Although the invention has been illustrated and described in more detail by the preferred exemplary embodiment, the invention is not restricted to the disclosed examples and other variations can be derived therefrom by a person skilled in the art without departing from the scope of protection of the invention.

The following, which may aid the reader in the perusal of the specification, is a list of reference numerals used in the above description:

1 Apparatus
2 Transmitter assembly
3 Patient's table
4 Navigation space
5 Generator coil
6 Connecting line
7 Actuating unit
8 Generator coil
10 Medical instrument
11 Receiver assembly
12 Sensor coil
13 Processing unit
14 Wireless link
16 Transmitter assembly
17 Receiver assembly
18 Location of the sensor coil
19 Source location
20 Direction
21 Field line direction
22 Field line direction
23 Center
24 Center
25 Distance
26 Distance
27 Hypotenuse

The invention claimed is:

1. An apparatus for determining positional information of a medical instrument, the apparatus comprising:

a processing unit, a plurality of first components configured to produce electromagnetic fields, said first components being transmitter coils;

a plurality of second components disposed and configured to measure relative field strengths of the electromagnetic fields produced by said plurality of first components and to transmit respective measurements to said processing unit, said second components being sensor coils;

said processing unit being configured to:

successively energize said transmitter coils in sequence to cause said transmitter coils to generate short magnetic pulses to be sensed by said sensor coils and to be output as measurement results;

determine a position of at least one first component of the plurality of first components or at least one second component of the plurality of second components based on the measurement results;

calculate, from sequentially induced measurement signals in respective said sensor coils, direction lines representing a direction or a direction component of a position of a respective transmitter coil of said transmitter coils relative to a respective sensor coil of said sensor coils; and determine a common point of intersection between the direction lines and determine the position of the at least one first component or the at least one second component to coincide with the common point of intersection without measuring a distance between the at least one first component and the at least one second component.

2. The apparatus according to claim 1, wherein:

said transmitter coils form at least two spaced-apart transmitter assemblies to be placed at defined locations in a reference system, each of said transmitter assemblies including a plurality of coils, each configured for actuation to produce a pulsed electromagnetic field;

said second component comprising at least one receiver assembly associated with the medical instrument, said at least one receiver assembly including at least two of said sensor coils; and said processing unit is configured to determine a position and/or an orientation of said at least one receiver assembly.

3. The apparatus according to claim 2, wherein said plurality of coils of each of said transmitter assemblies are arranged in defined positions relative to one another and said sensor coils of said receiver assembly are arranged in defined positions relative to one another.

4. The apparatus according to claim 3, wherein said plurality of coils are arranged directly adjacent one another and said sensor coils are arranged directly adjacent one another.

5. The apparatus according to claim 2, wherein each of said transmitter assemblies comprises at least two of said plurality of coils disposed orthogonally to one another.

6. The apparatus according to claim 2, wherein said at least one receiver assembly comprises said at least two sensor coils disposed orthogonally to one another.

7. The apparatus according to claim 1, wherein:

said transmitter coils form at least one transmitter assembly associated with the medical instrument, each of said transmitter coils being configured for actuation to produce a pulsed electromagnetic field;

said sensor coils form at least two spaced-apart receiver assemblies to be placed at defined locations in a reference system, each of said at least two receiver assemblies including a number of said sensor coils; and said processing unit is configured to determine a position and/or an orientation of the at least one transmitter assembly.

8. The apparatus according to claim 7, wherein said transmitter coils of said at least one transmitter assembly are arranged in defined positions relative to one another and said sensor coils of each of said at least two receiver assemblies are arranged in defined positions relative to one another.

9. The apparatus according to claim 8, wherein said transmitter coils are arranged directly adjacent one another and said sensor coils are arranged directly adjacent one another.

10. The apparatus according to claim 7, wherein each of said at least two receiver assemblies comprises at least two of said sensor coils.

11. The apparatus according to claim 10, wherein said sensor coils are disposed orthogonally to one another.

12. The apparatus according to claim 7, wherein said at least one transmitter assembly or said at least two receiver assemblies are integrated in the medical instrument and/or arranged at defined points in the reference system at mutually spaced-apart locations.

13. A method of determining positional information for a medical instrument, the method comprising the following steps:

generating electromagnetic fields with a plurality of transmitter coils by successively energizing the transmitter coils in sequence and generating with the plurality of transmitter coils short magnetic pulses, and measuring relative field strengths of the electromagnetic fields generated by the transmitter coils with a plurality of sensor coils and generating measurement results;

transmitting the measurement results to a processing unit;

receiving the measurement results in the processing unit and ascertaining direction information by way of direction finding on a basis of the measurement results; and determining a position of at least one transmitter coil of the plurality of transmitter coils or at least one sensor coil of the plurality of sensor coils by way of the direction information obtained in the ascertaining step by calculating, from sequentially induced measurement signals in respective sensor coils, direction lines representing a direction or a direction component of a position of a respective transmitter coil of the plurality of transmitter coils relative to a respective sensor coil of the plurality of sensor coils; and determining a common point of intersection between the direction lines and determining the position of the at least one transmitter coil or the at least one sensor coil to coincide with the common point of intersection without measuring a distance between the at least one transmitter coil and the at least one sensor coil.

14. The method according to claim 13, which comprises:

generating the electromagnetic fields as pulsed electromagnetic fields by driving the plurality of the transmitters coils of at least two spaced-apart transmitter assemblies positioned at defined locations in a reference system;

measuring a field strength of the pulsed electromagnetic fields with at least two of the plurality of sensor coils of at least one receiver assembly associated with the medical instrument; and determining a position and/or orientation of the at least one receiver assembly associated with the medical instrument.

15. The method according to claim 13, which comprises:
generating the electromagnetic fields as pulsed electromagnetic fields by driving the plurality of transmitter coils of at least one transmitter assembly associated with the medical instrument;
measuring a field strength of the pulsed electromagnetic field with the plurality of sensor coils of at least two mutually spaced-apart receiver assemblies placed at defined locations of a reference system; and
determining a position and/or orientation of the at least one transmitter assembly associated with the medical instrument.

16. The method according to claim 13, which comprises ascertaining the direction information on the basis of a dependency of a relative field strength on a direction orientation of a respective sensor coil in relation to the transmitter coil that produces the respective measured pulsed electromagnetic field.

17. The method according to claim 13, which comprises operating a number of the plurality of transmitter coils of a transmitter assembly and/or a number of the plurality of transmitter coils of different transmitter assemblies in succession.

18. A non-transitory computer-readable medium for determining a position of a medical instrument, wherein electromagnetic fields are produced by pulsed operation of a plurality of sequentially energized transmitter coils, relative field strengths of the electromagnetic fields thus produced are measured by using a plurality of sensor coils, and measurement results thus obtained are transmitted to a processing unit, the non-transitory computer-readable medium comprising:
computer-executable instructions stored in non-transitory form for ascertaining direction information by position finding based on the measurement results; and
computer-executable instructions for determining a position of at least one of the plurality of transmitter coils or at least one of the plurality of sensor coils by using the direction information obtained by calculating, from sequentially induced measurement signals in respective said sensor coils, direction lines representing a direction or a direction component of a position of a respective transmitter coil relative to a respective sensor coil, and by ascertaining the position of the respective transmitter coil or the respective sensor coil by determining a common point of intersection between the direction lines without measuring a distance between the respective transmitter coil and the respective sensor coil;
wherein the computer-executable instructions are executed on the processing unit.

* * * * *